(12) United States Patent
Izbicki et al.

(10) Patent No.: US 7,132,288 B2
(45) Date of Patent: Nov. 7, 2006

(54) MEDIUM FOR CULTURING TUMOR CELLS

(75) Inventors: Jakob Izbicki, Hamburg (DE); Stefan Hosch, Neuss (DE); Peter Scheunemann, Hamburg (DE)

(73) Assignee: Uni-Klinikum Hamburg-Eppendorf, Hamburg (DE)

( * ) Notice: Subject to any disclaimer, the term of this patent is extended or adjusted under 35 U.S.C. 154(b) by 410 days.

(21) Appl. No.: 10/467,982

(22) PCT Filed: Feb. 14, 2002

(86) PCT No.: PCT/DE02/00532

§ 371 (c)(1),
(2), (4) Date: Aug. 13, 2003

(87) PCT Pub. No.: WO02/064754

PCT Pub. Date: Aug. 22, 2002

(65) Prior Publication Data
US 2004/0067581 A1 Apr. 8, 2004

(30) Foreign Application Priority Data
Feb. 14, 2001 (DE) .................. 101 06 826

(51) Int. Cl.
*C12N 5/00* (2006.01)
(52) U.S. Cl. .................. 435/406; 435/325; 435/366; 435/372; 435/372.1; 435/404; 435/405; 435/407
(58) Field of Classification Search .............. 435/406, 435/405, 404, 407, 408, 372, 372.1, 366, 435/325
See application file for complete search history.

(56) References Cited

U.S. PATENT DOCUMENTS 6,156,516 A * 12/2000 Nunokawa .................. 435/6

OTHER PUBLICATIONS

Hombauer, H., et al., "Selective Interactions Between Epithelial Tumour Cells and Bone Marrow Mesenchymal Stem Cells"; British Journal of Cancer (2000); 82 (7); 1290-1296.
Pantel, K., et al., "Establishment of Micromestastic Carcinoma Cell Lines: A Novel Source of Tumor Cell Vaccines"; Journal of the National Cancer Institute; vol. 87; No. 15, Aug. 2, 1995.
Hosch, S., et al., "Malignant Potential and Cytogenic Characteristics of Occult Disseminated Tumor Cells in Esophegeal Cancer"; Advances in Brief; pp. 6830-6840.
Kurec, A., et al., "Use of the APAAP Method in the Classification and Diagnosis of Hemotologic Disorders"; Clinics in Laboratory Medicine; vol. 7, No. 4 (1988) 223-236.
Gilles, et al., "The Epithelial to Mesenchymal Transition and Metastatic Progression in Carcinoma", The Breast Journal, vol. 2, No. 1, pp. 83-96, (1996).
Telenius, et al., "Cytogenic Analysis by Chromosome Painting Using DOP-PCR Amplified Flow-Sorted Chromosomes", Genes, Chromosomes & Cancer, vol. 4, pp. 257-263 (1992).

Byrne, J., et al., "The use of monoclonal antibodies for the histopathological detection of mammary axillary micrometastases." European Journal of Surgical Oncology, 1987, vol. 13, pp. 409-411.
Calaluce, Robert, et al. "Micrometastasis in Colorectal Carcinoma: A Review." 1998, vol. 67, pp. 194-202.
Latza, U., et al. "Ber-EP4: new monoclonal antibody which distinguishes epithalia from mesothelia." 1990, Journal of Clinical Pathology, 1990, vol. 43, pp. 213-219.
Liefers, Gerrit-Jan, et al. "Micrometastases and Survival in Stage II Colorectal Cancer." New England Journal of Medicine, 1998, vol. 339, pp. 223-228.
Pantel, K., et al. *Minimal Residual Epithelial Cancer: Diagnostic Approaches and Prognostic Relevance*. Gustav Fischer Verlag Publishing: Stuttgart. 1996.
Passlick, Bernward, et al. "Immunohistochemical Assessment of Individual Tumor Cells in Lymph Nodes of Patients With Non-Small-Cell Lung Cancer." Journal of Clinical Oncology, vol. 12, pp. 1827-1832.
Raymond, Wendy A., et al. "Immunoperoxidase Staining in the Detection of Lymph Node Metastases in Stage 1 Breast Cancer." Pathology, 1989, vol. 21, pp. 11-15.
Sidransky, David. "Nucleic Acid-Based Methods for the Detection of Cancer." Science, 1997, vol. 278, 1054-1058.
Hosch, Stefan B. "Early Lymphatic Tumor Cell Dissemination in Pancreatic Cancer: Frequency and Prognostic Significance." Pancreas, 1997, vol. 15, pp. 154-159.
Greenson, Joel K., et al. "Identification of Occult Micrometastases in Pericolic Lymph Nodes of Dukes' B Colorectal Cancer Patients Using Monoclonal Antibodies against Cytokeratin and CC49." CANCER, 1994, vol. 73, pp. 563-569.
Passlick, Berward, et al. "Detection of Disseminated Lung Cancer Cells in Lymph Nodes: Impact on Staging and Prognosis." Ann. Thorac. Surg., 1996, vol. 61, pp. 177-183.
Nevinny-Stickel, C., et al. "Nonradioactive HLA Class II Typing Using Polymerase Chain Reaction and Digoxigenin-11-2'-3'-dideoxy-uridinetriphosphate-Labeled Oligonucleotide Probes." Human Immunology, 1991, vol. 31, pp. 7-13.
Speicher, Michael R., et al. "Karyotyping human chromosomes by combinatorial multi-fluor FISH." Nature Genetics, 1996, vol. 12, pp. 368-375.

(Continued)

*Primary Examiner*—Leon B. Lankford, Jr.
(74) *Attorney, Agent, or Firm*—Steven J. Hultquist; Intellectual Property/Technology Law

(57) ABSTRACT

Disclosed is a medium for cultivating tumor cells, comprising the following constituents, as comprised for example in the medium RPMI 1640: (a) fetal calf serum (FCS), (b) penicillin-streptomycin, (c) L-glutamine, (d) transferrin, (e) insulin, (f) human epidermal growth factor (EGF) and (g) α-TGF. A method for characterizing tumor cells or potential tumor cells, respectively, is also described. Said method includes the culturing of cells in the inventive medium and the two tumor cell lines LNHOS1 and PTHOS1 established by means of the inventive culturing method.

14 Claims, No Drawings

OTHER PUBLICATIONS

Eils, R., et al. "An optimized, fully automated system for fast and accurate identification of chromosomal rearrangements by multiplex-FISH (M-FISH)." Cytogenet Cell Genet, 1998, vol. 82, pp. 160-171.

Lengauer, Christoph, et al. "Metaphase and Interphase Cytogenetics with Alu-PCR-amplified Yeast Artificial Chromosome Clones Containing the *BCR* Gene and the Protooncogenes c-*raf*-1, c-*fms*, and c-*erb*B2."Cancer Research, 1992, vol. 52, pp. 2590-2596.

Harris, Curtis C. "Structure and Function of the p53 Tumor Suppressor Gene: Clues for Rational Cancer Therapeutic Strategies." Journal of the National Cancer Institute, 1996, vol. 88, pp. 1442-1455.

Izbicki, Jakob Robert, et al. "Prognostic Value of Immunohistochemically Identifiable Tumor Cells in Lymph Nodes of Patients with Completely Resected Esophageal Cancer." New England Journal of Medicine, 1997, vol. 337, pp. 1188-1194.

* cited by examiner

MEDIUM FOR CULTURING TUMOR CELLS

CROSS-REFERENCE TO RELATED APPLICATIONS

This application is filed under the provisions of 35 U.S.C. §371 and claims the priority of International Patent Application No. PCT/DE02/00532 filed 14 Feb. 2002, which in turn claims priority of German Patent Application No. 101 06 826.3 filed 14 Feb. 2001.

BACKGROUND OF THE INVENTION

1. Field of the Invention

The present invention relates to a medium for cultivating tumor cells, comprising the following constituents: (a) fetal calf serum (FCS), (b) penicillin-streptomycin, (c) L-glutamine, (d) transferrin, (e) insulin, (f) human epidermal growth factor (EGF) and (g) α-transforming growth factor (α-TGF). Furthermore, the present invention relates to a method for characterizing tumor cells or potential tumor cells, respectively, comprising the culturing of cells in the inventive medium, and the two tumor cell lines LNHOS1 and PTHOS1 established by means of the inventive culturing method.

2. Description of Related Art

Due to the use of immunohistochemical and molecular-biological examination techniques it has become possible to identify epithelial tumor cells in lymph nodes (Byrne et al., J. Surg. Oncol. 13 (1987), 409–411; Calaluce et al., J.Surg.Oncol. 67 (1998), 194–202; Latza et al., J.Clin.Pathol. 43 (1990), 213–219; Liefers et al., NEJM 339 (1998), 223–228; Pantel et al., Prog.Histochem.Cytochem. 30 (1996), 1–60; Passlick et al., J. Clin. Oncol. 12 (1994), 1827–1832; Raymond et al., Pathology 21 (1989), 11–50; and Sidransky, Science 278 (1997), 1054–1059). However, despite a growing number of publications which were able to prove a prognostic relevance of nodal early disseminated tumor cells in patients with carcinomas of the lungs, breasts, prostrate and the gastrointestinal tract (Izbicki et al., NEJM 337 (1997), 1188–1194; Hosch et al., Pancreas 15 (1997), 154–159; Passlick et al., J.Clin.Oncol. 12 (1994), 1827–1832; Greenson et al., Cancer 73 (1994), 563–569; and Liefers et al., NEJM 339 (1998), 223–228), the biological relevance of immunohistochemically detectable individual tumor cells remains unclear. This is due to the fact that so far it is almost impossible to further characterize these cells due to their extremely low frequency (1 tumor cell against the background of $10^4$–$10^5$ normal lymph node cells). The uncertainty accompanying previous examination methods whether individual tumor cells are tumorigenic micrometastases or merely scaled-off and avital cells of the primary tumor presently prevents the introduction of this parameter into the international "tumor staging" nomenclature, i.e., it also does not permit making any prognoses or taking therapeutic measures which may be necessary.

Thus it is the underlying object of the present invention to solve the technical problem of overcoming these drawbacks of the methods used in the prior art, i.e., to provide means which allow identification whether the potential tumor cells in a tissue sample represent viable and malign tumor cells.

SUMMARY OF THE INVENTION

The solution to this problem is reached by providing the embodiments characterized in the claims.

Surprisingly, it has been found that cells with an unclear status as to vitality and tumor generation can be multiplied in the inventive medium and further examined as to possible tumor generation. For this purpose tissue samples from a conventionally histopathologically tumor-free, but immunohistochemically positive lymph node of a patient with an esophageal adenocarcinoma were cultivated in the inventive medium to be better able to examine the biology of the early disseminated tumor cells in lymph nodes. It was possible to establish a permanent cell line (LNHOS1). By culturing in the inventive medium the establishment of a permanent cell line from the autologous primary tumor of the patient was also successfully achieved (PTHOS1). For comparison, both cell lines were more closely characterized by the use of micro-satellite analysis and HLA-DRBI* typing, multiplex-fluorescence in situ hybridization (M-FISH), fluorescence-activated flow cytometry (FACS) and ELISA technique. For the cell line LNHOS1 generated from the lymph node the results of these analyses showed tumor-specific cytogenetic alterations as well as the expression of proteins associated with metastasing. Moreover, upon xeno-transplantation onto immunodeficient SCID mice, it was shown that this cell line is tumorigenic and metastatic. Thus, for the first time the direct proof has been produced by means of the inventive cell line LNHOS1 that the immunohistochemically detectable individual tumor cells (occultly disseminated tumor cells) definitely are vital and malign tumor cells. On the one hand the evidence of a permanent expansion of "occult tumor cells", which was enabled by means of culturing in the inventive medium, proves that such cells can be cells with an unlimited proliferative in vitro potential, on the other hand these in vivo cells in the SCID mouse model exhibit tumorigenic and metastatic potential. Thus, important information on the biological properties of early disseminated tumor cells can be obtained by means of further analyses of such cell lines, which is useful with regard to an optionally required therapy of a minimal residual tumor disease and moreover, respectively, to develop new strategies to detect and treat such diseases.

Particularly, the present invention relates to a medium for cultivating tumor cells, characterized in that it comprises the following constituents: (a) fetal calf serum (FCS), (b) penicillin-streptomycin, (c) L-glutamine, (d) transferrin, (e) insulin, (f) human epidermal growth factor (EGF), and (g) α-transforming growth factor (α-TGF) The suitable concentrations of the individual constituents are easily determined by the person skilled in the art, with the individual constituents of the inventive medium being present in the following concentrations in a preferred embodiment: (a) 2–20% of fetal calf serum (FCS), (b) 20–2000 U/ml of penicillin-streptomycin, (c) 0.2–20 mM of L-glutamine, (d) 2–200 µg/ml of transferring, (e) 0.5–50 µg/ml of insulin, (f) 2–200 ng/ml of human epidermal growth factor (EGF), and (g) 2–200 ng/ml of α-TGF.

Optionally, the medium may comprise further constituents, such as "basic fibroblast growth factor", cytokines (for example, interleukins, interferon) or other growth factors.

A medium according to the invention with the following concentrations of the individual constituents is particularly preferred: (a) 10% of fetal calf serum (FCS), (b) 200 IU/ml of penicillin-streptomycin, (c) 2 mM of L-glutamine, (d) 20 µg/ml of (human) transferrin, (e) 5 µg/ml of (bovine) insulin, (f) 50 ng/ml of (recombinant) human epidermal growth factor (EGF), and (g) 20 ng/ml of α-TGF.

The "base medium" to which the inventive constituents are added may be any medium which is conventionally used for culturing animal cells, preferably mammalian cells, for example RPMI 1640+5–20% FCS (cf. DSMZ catalogue, Human and Animal Cell Lines, 1999) or TUM medium.

In a preferred embodiment of the inventive medium the "base medium" containing the above-mentioned constituents (a) to (g) is the RPMI-1640 medium (Life Technologies, Paisley, Scotland).

The inventive medium offers the advantage that after disaggregation of e.g. lymph node samples a monolayer formation of at first fibroblastoid cells was regularly observed. After incubating for 3 to 6 weeks tumor cell nests were identified. Moreover, it was observed that a close spatial relationship existed between these tumor cells and the fibroblastoid cells, which implies that these co-cultivated cells favourably influence the growth of the tumor cells by functioning as "by-stander" cells.

The present invention also relates to a method for characterizing tumor cells or supposed tumor cells, respectively, which is characterized in that the cells are cultivated in the inventive medium under suitable conditions, optionally by (partially) renewing the medium at suitable intervals of time, that the cells are harvested and subsequently characterized. Suitable conditions, for example as to suitable containers, temperature, relative humidity, $O_2$-content and $CO_2$-content of the gas phase, are known to the person skilled in the art. Preferably, the tumor cells or the supposed tumor cells, respectively, are cultivated in the inventive medium under the following conditions: (a) 37° C., (b) 100% relative humidity, (c) 10% of $O_2$, and (d) 5% of $CO_2$. Suitable methods for the (genotypic and phenotypic) characterization of the cells which allow statements as to their possible tumorigenic and/or metastasis-forming potential are known to the skilled person. These include, for example, the in vitro and in vivo methods described in Example 2 specified below.

Finally, the present invention relates to the two cell lines LNHOS1 und PTHOS1 established by means of culturing in the inventive medium.

According to the Budapest Treaty the following cell cultures were deposited at the Deutsche Sammlung von Mikroorganismen und Zellkulturen GmbH (DSMZ) [German Type Collection of Microorganisms and Cell Cultures], Mascheroder Weg 1b, 38124 Braunschweig, Germany:

| Cell culture LN HOS1 | DSM ACC2472 | Nov. 2, 2000 |
| Cell culture PT HOS1 | DSM ACC2371 | Sep. 14, 2000 |

DETAILED DESCRIPTION OF THE INVENTION

The invention will be explained on the basis of the following examples.

EXAMPLE 1

Establishing Cell Lines PTHOS1 and LNHOS1

Immediately upon sampling the operation specimen, which came from a patient with esophageal cancer (stage $pT_pN_1M_0$ according to the international "tumor staging" nomenclature), tissue samples were taken from the primary tumor and five different lymph node stations which were named according to a mapping scheme. Next, each of the lymph nodes was halved, as described in Izbicki et al., NEJM 337 (1997), 1188–1194. One half of the lymph node was sent to the routine histopathological assessment while the other half and the primary tumor sample were quick-frozen in liquid nitrogen for the immunohistochemical analyses and kept at −80° C. until further treatment. Additionally, samples for the cell culture were taken from one of the macroscopically inconspicuous lymph nodes on the left gastric artery. These tissue samples were cut into small pieces, repeatedly washed in the medium RPMI-1640 (Life Technologies, Paisley, Scotland) and disaggregated into single-cell suspensions by means of a "medi-machine" (DAKO, Hamburg). The cell suspensions were incubated at 37° C. and 5% of $CO_2$ in the incubator (incubator B 5061, Heraeus, Munich, Germany) in T25 cell culture vials coated with extracellular matrix (ECM). The expansion of these cell lines followed in the RPMI-1640 medium supplemented by the following constituents: 10% of fetal calf serum (FCS; c.c.pro, Neustadt, Germany), 200 U/ml of penicillin-streptomycin (initial concentration: 10000 U/ml; Life Technologies, Karlsruhe, Germany), 2 mM of L-glutamine (initial concentration: 200 mM; Life Technologies, Karlsruhe, Germany), 20 µg/ml of transferrin (Boehringer, Mannheim, Germany), 5 µg/ml of insulin (Boehringer, Mannheim, Germany), 20 ng/ml of human epidermal growth factor (EGF) (PBH, Hanover, Germany), and 20 ng/ml of α-TGF. The dilution of α-TGF required for the addition to the medium took place in PBS supplemented by 1% of bovine serum albumin (BSA). So far these cell lines have been permanently expanded over 70 passages and can thus be said to be immortal.

EXAMPLE 2

Characterization of PTHOS1 and LNHOS1 as Tumorigenic and Metastatic Cell Lines

In the lymph node sample cryopreserved for immunohistochemical analyses 3 individual tumor cells could be identified by means of the APAAP technique against the background of about $10^5$ normal lymph node cells. For this purpose, cryo sections were fixed for one minute in cold acetone of +4° C. after one hour of air drying and subsequently rehydrated in TRIS-buffered physiological saline solution (TBS, pH 7.4). Then, the specimen were diluted 1:10 for 20 minutes with AB serum (Biotest Diagnostics 805135, Dreieich, Germany) in TBS and incubated to prevent an unspecified background coloring. Next came incubation with the monoclonal anti-epithelial cell antibody Ber-EP4 (Code No. M0804, Dako, Hamburg; Latza et al., J.Clin.Pathol. 43 (1990), 213–219) in a dilution of 1:400 in TBS (0.625 µg/ml). After washing in TBS three times for 5 minutes each a rabbit anti-mouse Ig bridge antibody (Code No. Z0259, Dako, Hamburg), diluted 1:50 in TBS (64 µg/ml) for 30 minutes, was incubated. After another washing for 3×5 minutes in TBS the APAAP complex (Code No. D0651, Dako, Hamburg) was applied for 30 minutes in a dilution of 1:100 in TBS (0.9 µg/ml). The antibody reaction was illustrated by means of new fuchsin (cf. APAAP substrate preparation). After incubating the section specimen for thirty minutes in the substrate a single washing in distilled water and the nuclear counterstain with Gill's hematoxylin for 30 seconds took place (Passlick et al., Ann. Thorac. Surg. 61, p. 77–83 (1996)).

The autologous origin of both cell lines was confirmed by means of a microsatellite analysis for which the "GenePrint Fluorescent CTTV STR™ Multiplex Systems" kit of Promega (Madison, Wis., USA) was used. During the electrophoretic fractioning on polyacrylamide gels all DNA amplificates showed an identical microsatellite band pattern. In order to exclude contamination during passage and change of medium through heterologous cells, several HLA-DRBI* typings were carried out according to the "oligonucleotide typing" system by Nevinny-Stickel et al. (Hum. Immunol. 31: p. 7–13 (1991)).

In all cases the cell lines and the sublines showed an identical genotype.

In addition to this, both cell lines were cytogenetically characterized to great extent by using the M-FISH technique. This technique allows the simultaneous depiction of all human chromosomes in various colors (Speicher et al., Nature Genetics, 12 (1996), p. 368–375; Eils et al., Cytogenet. Cell Genet., 82 (3–4), p. 160–171 (1998)). For the analysis metaphase chromosomes of the cell lines are prepared. The procedure is carried out according to standard protocols. The spread-out metaphases are pretreated with RNase and pepsin (Lengauer et al., Cancer Res. 52, p. 2590–2596 (1992)). The subsequent M-FISH analysis is carried out as described in Speicher et al. (1996, see above) and Eils et al. (1998, see above). "Whole chromosome painting" probes (J. Wienberger, Cambridge) obtained by flow cytometry are amplified following a standard DOP-PCR protocol (Telenius et al., Genes Chromosomes Cancer, (1992), 4, p. 257–263). In order to be able to depict all 24 human chromosomes in various colors, 5 different probe pools are produced (each by itself directed against a different complement of chromosomes) and marked by using a DOP-PCR assay with various fluorochromes (Eils et al., 1998, see above). Cot-1 DNA and salmon sperm DNA are added during the ethanol precipitation of these probes. The hybridisation of the probe mix with the target DNA to be analyzed takes 2 days. The hybridization results were visualized according to a standard protocol (Speicher et al., 1996, see above; Eils et al., 1998, see above). The evaluation and documentation can be made using a Leica DMRXA-RF8 microscope fitted with a Sensys camera (Photometrics, Tucson, USA) and Leica software (Leica Microsystems Imaging Solutions Ltd., Cambridge, Great Britain). The results can be shown in digital fast color images as well as in pseudocolor images (Eils et al., 1998, see above).

The obtained result showed that both cell lines have a hypertriploid chromosome complement. Some structural changes, such as del(5)(q1?3q2?22), der(8), der(9)del(9)(p21-22)del(9)(q21-22), der(17), der(22)t(19;22) and the loss of the Y chromosome were proven in all or most of the examined metaphase specimens of both cell lines. Further aberrations such as der(1)t(1;20), der(3)t(3;17), der(8)t(5;8), der(10)t(1;10) and der(13)t(5;13) were exclusively observed in about 50% of all metaphase spreadings of PTHOS1 cells, whereas LNHOS1 cells did not show these chromosomal anomalies. On the other hand a further structural change, that is, an insertion of chromosome 13 material into the short arm of chromosome 1 [ins(1;13)(p22;q?)], could be detected exclusively in LNHOS1 cells. By comparison, PTHOS1 cells did not show this change. Judging by the DAPI banded structure this inserted chromosome 13 material probably originates from a light G band.

Furthermore, an extensive phenotypic characterization of both cell lines through indirect immunofluorescence technique by use of a "FACScan cell sorter" (Becton Dickinson., San Jose, Calif., USA) was carried out (see Table 1). In order to confirm the epithelial origin of both established cell lines the expression of histogenesis markers such as cytokeratins, vimentin, α-smooth-muscle actin and endothelial antigens (factor VIII, EN-4) was analyzed by means of flow cytometry. In harmony with the undifferentiation of the primary tumor in situ no expression of epithelial cytoskeleton proteins (cytokeratins) for PTHOS1 with the monoclonal anti-cytokeratin antibodies (mAk) A45B/B3 (Micromet, Munich), AE1/AE3 (DAKO, Hamburg), CK2 (Roche Diagnostics, Mannheim) and LP34 5D3 (Medac, Hamburg) could be detected, whereas LNHOS1 showed a heterogeneous expression profile. Neither PTHOS1 cells nor LNHOS1 cells reacted with the mAk against endothelial cells or α-smooth-muscle actin, whereas the mesenchymal cytoskeleton protein vimentin was expressed heterogeneously by both cell lines. This seems to indicate an "epithelial to mesenchymal transition" (EMT) which is accompanied by an increase in motility of carcinoma cells (Gilles et al., Breast J. 2 (1996), 83–96). Furthermore, the expression of proteins of the E-cadherin cadenin complex, which is mainly responsible for the homotypical cell—cell adhesion of epithelial cells, points to the epithelial origin of both cell lines. On the other hand, the epithelial cell adhesive molecule EpCAM (17-1A) is expressed by only one LNHOS1 subpopulation, whereas PTHOS1 cells do not express this molecule. Both cell lines show characteristic features of malign tumor cells, such as the overexpression of the erbB2 oncogene product $p185^{erbB2}$ and the p53 tumor suppressor gene product. The overexpression of erbB2 and accumulation of the p53 protein are frequent changes in epithelial tumors including the esophageal carcinoma. Moreover, as an overexpression of p53 is often caused by mutations of the p53 gene, the p53 genes of both cell lines were sequenced. In doing so, a single-point mutation was identified in codon 176 [CGC(Arg)→CAC(His)]—a "hot spot" region—which causes the expression of a stabilized p53 protein (Harris, JNCI 88 (1996), 1442–1455).

Furthermore, the expression of molecules of the two cell lines was examined, which in some tumor entities are involved in the process of progression and metastasing. In this connection adhesive molecules play a crucial role through the mediation of heterotypical and homotypical cell—cell and cell-matrix interactions, respectively. As far as the cell-matrix adhesive molecules were concerned, an expression of $α_5$ -(CD49e), $α_6$ -(CD49f) and $β_1$-integrin subunits could be identified on both cell lines, whereas the integrin subunits $α_v$ (CD51), $β_2$ (CD18) and $β_3$ (CD61) were neither expressed by LNHOS1 cells nor by PTHOS1 cells. It is interesting that contrary to that, the $β_4$-integrin subunit (CD104) was expressed exclusively by an LNHOS1 subfraction. A further cell-matrix adhesive molecule, the 67 kD laminin receptor (67LR), was also expressed exclusively by an LNHOS1 subpopulation. This receptor plays an important role for the interaction between tumor cells and the basal membrane. Although E-cadherin and its intracytoplasmic ligands α- and γ-catenin (plakoglobin) were expressed by both cell lines, desmoglein (DMG) as the most important component of the desmosomal membrane nucleus was again expressed only by a subpopulation of LNHOS1 cells, while PTHOS1 cells did not show any expression of desmoglein. A different expression between PTHOS1 cells and LNHOS1 cells was also detected for the adhesive molecules of the immunoglobulin superfamily. While both cell lines proved positive for LFA-3 (CD58) and negative for KAI-1 (CD82), VCAM-1 (CD106) and Muc-18 (CD146) in the flow cytometry analysis, a neoexpression of ICAM-1 (CD54), which is usually expressed only by lymphoid and myeloid cells, could again only be identified on a LNHOS1 subpopulation comprising 25%.

In addition to cell—cell and cell-matrix interactions, which are mediated through adhesive molecules, tumor cells need the ability to proteolytically degrade the extracellular matrix (ECM) to wander through the surrounding stroma. In this connection metallomatrix proteases (MMPs) and their inhibitors play an important role. MMPs allow cell migration through degradation and regulation of specific ECM components, such as laminin, collagen, fibronectin or vitronectin, and are themselves inhibited by the binding of "tissue inhibitors of metalloproteases (TIMPs)". Both cell lines expressed MMP-9 (gelatinase B), MMP-14 (MT-MMP) as well as TIMP-1, whereas no expression of MMP-2 (gelatinase A), MMP-3 (stromelysin) or TIMP-2 was detectable for PTHOS1 nor for LNHOS1. The analysis of the blood-type antigen Lewis Y ($Le^y$), which is frequently overexpressed on tumors, could also identify an expression only in a subpopulation of LNHOS1 cells.

In order to verify the tumorigenic potential of P-THOS1 cells and LNHOS1 cells in vivo, between $1 \times 10^5$ and $6.5 \times 10^6$ tumor cells were injected subcutaneously (s.c.) into the flanks of immunodeficient SCID mice. After an observation period of 2 to 29 weeks all 20 mice which had been administered PTHOS1 cells, and 7 of 8 mice which had been administered LNHOS1 cells developed local tumors in the area of the application point. Local tumor formations were clearly visible at an earlier point in time after the injection of PTHOS1 cells than after the injection of LNHOS1 cells (4.7 vs. 13.9 weeks on average, p=0.0001). Likewise, PTHOS1 cells needed distinctly less time (8.6 vs. 18.7 weeks on average, p=0.002) than LNHOS1 cells to develop local tumors of maximum size (>15 mm on average). In two animals of each group a local tumor penetration through the peritoneum into the abdominal cavity occurred, while no macroscopic metastasing could be proven autoptically in any case. On the other hand, the immunohistochemical evidence of pulmonary micrometastasing as well as the regeneration of several cell lines from various mouse organs (mesenterial lymph nodes, bone marrow, lungs) was achieved.

TABLE 1

Phenotypic Characteristics of the Cell Lines LNHOS1 and PTHOS1

| Antigen Family | positive | negative |
| --- | --- | --- |
| epithelial adhesion molecules | E-cadherin (desmoglein*) α-catenin plakoglobin (EpCAM*) Muc-1 (67 kD laminin receptor*) | |
| integrins | $α_5$ $α_6$ $(β_1*)$ | $α_v$ $β_2$ $β_3$ |
| Ig superfamily | (ICAM-1*) LFA-3 | KAI-1 VCAM-1 1Muc-18 |
| Metallomatrix proteinases and inhibitors | MMP-9 MMP-14 TIMP-1 | MMP-2 MMP-3 TIMP-2 |
| proto onco gene/ suppressor gene products | erbB2 (p53) | EGF-R |
| histogenesis markers | (cytokeratins*) (vimentin) | α-smooth muscle actin factor VIII EN-4 |
| other molecules | $β_2$ microglobulin (Lewis Y*) | |

( ), heterogeneous population with positive and negative cells
*molecules exclusively expressed by LNHOS1 cells

We claim:
1. A medium for cultivating tumor cells, comprising the following constituents:
   (a) fetal calf serum (FCS);
   (b) penicillin-streptomycin;
   (c) L-glutamine;
   (d) transferrin;
   (e) insulin;
   (f) human epidermal growth factor (EGF); and
   (g) α-TGF.
2. The medium according to claim 1, wherein the constituents (a) to (g) are present in the following concentrations:
   (a) 2–20%;
   (b) 20–2000 U/ml;
   (c) 0.2–20 mM;
   (d) 2–200 µg/ml;
   (e) 0.5–50 µg/ml;
   (f) 2–200 ng/ml; and
   (g) 2–200 ng/ml.
3. The medium according to claim 2, wherein the constituents (a) to (g) are present in the following concentrations:
   (a) 10%;
   (b) 200 U/ml;
   (c) 2 mM;
   (d) 20 µg/ml;
   (e) 5 µg/ml;
   (f) 50 ng/ml; and
   (g) 20 ng/ml.
4. The medium according to claim 1, further comprising a base medium for the addition of constituents (a) to (g), wherein said base medium comprises medium RPMI 1640.
5. A method for characterizing tumor cells or potential tumor cells, said method comprising culturing the cells in a medium according to claim 1, harvesting the cells, and characterizing the cells.
6. The method according to claim 5, wherein the tumor cells are cultivated under the following conditions:
   (a) 37° C.;
   (b) 100% relative humidity;
   (c) 10% of $O_2$; and
   (d) 5% of $CO_2$.
7. The medium according to claim 2, further comprising a base medium for the addition of constituents (a) to (g), wherein said base medium comprises medium RPMI 1640.
8. The medium according to claim 3, further comprising a base medium for the addition of constituents (a) to (g), wherein said base medium comprises medium RPMI 1640.
9. The method according to claim 5, wherein the medium comprises the constituents (a) to (g) in the following concentrations:
   (a) 2–20%;
   (b) 20–2000 U/ml;
   (c) 0.2–20 mM;
   (d) 2–200 µg/ml;
   (e) 0.5–50 µg/ml;
   (f) 2–200 ng/ml; and
   (g) 2–200 ng/ml.
10. The method according to claim 5, wherein the medium comprises the constituents (a) to (g) in the following concentrations:
   (a) 10%;
   (b) 200 U/ml;
   (c) 2 mM;
   (d) 20 µg/ml;
   (e) 5 µg/ml;

(f) 50 ng/ml; and
(g) 20 ng/ml.

11. The method according to claim 5, wherein the medium comprises a base medium for the addition of constituents (a) to (g), wherein said base medium comprises medium RPMI 1640.

12. The method according to claim 5, wherein the characterizing step comprises genotypic characterization of the cells.

13. The method according to claim 5, wherein the characterizing step comprises phenotypic characterization of the cells.

14. The method according to claim 5, wherein the characterizing step comprises characterization of the cells as to their potential tumorigenic and/or metastasis-forming character.

* * * * *